United States Patent
Stupp et al.

(10) Patent No.: US 8,940,858 B2
(45) Date of Patent: Jan. 27, 2015

(54) FIBROUS MICROCAPSULES AND METHODS OF ASSEMBLY AND USE THEREOF

(75) Inventors: Samuel Stupp, Chicago, IL (US); Dorota Rozkiewicz, Chicago, IL (US)

(73) Assignee: Northwestern University, Evanston, IL (US)

( * ) Notice: Subject to any disclaimer, the term of this patent is extended or adjusted under 35 U.S.C. 154(b) by 434 days.

(21) Appl. No.: 13/109,186

(22) Filed: May 17, 2011

(65) Prior Publication Data

US 2011/0280944 A1 Nov. 17, 2011

Related U.S. Application Data

(60) Provisional application No. 61/345,419, filed on May 17, 2010.

(51) Int. Cl.
| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 9/50 | (2006.01) |
| A61K 48/00 | (2006.01) |

(52) U.S. Cl.
CPC .............. *A61K 9/5036* (2013.01); *A61K 9/5052* (2013.01); *A61K 9/5089* (2013.01); *A61K 48/00* (2013.01)
USPC .......................................................... 530/300

(58) Field of Classification Search
None
See application file for complete search history.

(56) References Cited

U.S. PATENT DOCUMENTS

| | | | |
|---|---|---|---|
| 6,455,052 B1 * | 9/2002 | Marcussen et al. ........ | 424/234.1 |
| 7,267,120 B2 | 9/2007 | Rustad et al. | |
| 7,332,286 B2 | 2/2008 | Diamond | |
| 7,849,851 B2 | 12/2010 | Zierenberg et al. | |
| 7,905,228 B2 | 3/2011 | Blacker et al. | |
| 8,138,140 B2 * | 3/2012 | Stupp et al. .................. | 514/1.1 |
| 8,512,693 B2 * | 8/2013 | Capito et al. ................. | 424/93.1 |
| 2008/0199431 A1 * | 8/2008 | Capito et al. ................. | 424/93.1 |

OTHER PUBLICATIONS

Zhang. Building from the botoom up. Materials Today, May 2003 vol. 6, Issue 5, pp. 20-27.*

Vauthey et al. Molecular self-assembly of surfactant-like peptides to form nanotubes and nanovesicles. PNAS, Apr. 2002. vol. 99, No. 8, pp. 5355-5360.*

Tu et al. Liposomal Targeting Through Peptide-Amphiphile Functionalization. American Pharmaceutical Review. 2004, vol. 7, Issue 2, pp. 36-41.*

Torchilin. Recent Advances With Liposomes as Pharmaceutical Carriers. Nature Reviews, Drug Discovery. 2005, vol. 4, pp. 145-160.*

Capito et al., "Self-assembly of large and small molecules into hierarchically ordered sacs and membranes," Science, 319: 1812-1816 (2008).

Caruso et al., "Nanoengineering of inorganic and hybrid hollow spheres by colloidal templating," Science, 282: 1111-1114 (1998).

Chang, "Semipermeable Microcapsules," Science, 146: 524-525 (1964).

Decher, "Fuzzy Nanoassemblies:Toward Layered PolymericMulticomposites," Science, 277: 1232-1237 (1997).

Donath et al., "Novel Hollow Polymer Shells by Colloid-Templated Assembly of Polyelectrolytes," Angew Chem Int Ed, 37: 2202-2205 (1998).

Hartgerink et al., "Peptide-amphiphile nanofibers: a versatile scaffold for the preparation of self-assembling materials," PNAS, 99: 5133-5138 (2002).

Hartgerink et al., "Self-assembly and mineralization of peptide-amphiphile nanofibers," Science, 294: 1684-1688 (2001).

Hirabayashi et al., "Charged droplet formation in sonic spray," Int J. Mass Spectrom Ion Process, 175: 277-282 (1998).

Kamio et al., "Microcapsules with macroholes prepared by the competitive adsorption of surfactants on emulsion droplet surfaces," Langmuir, 24: 13287-13298 (2008).

Kenis et al., "Microfabrication inside capillaries using multiphase laminar flow patterning," Science, 285: 83-85 (1999).

Rajangam et al., "Heparin binding nanostructures to promote growth of blood vessels," Nano Lett, 6: 2086-2090 (2006).

Silva et al., "Selective differentiation of neural progenitor cells by high-epitope density nanofibers," Science, 303: 1352-1355 (2004).

Steinleitner et al., "An evaluation of Flowgel as an intraperitoneal barrier for prevention of postsurgical adhesion reformation," Fertility & Sterility, 57: 305-308 (1992).

Steinleitner et al., "Poloxamer 407 as an intraperitoneal barrier material for the prevention of postsurgical adhesion formation and reformation in rodent models for reproductive surgery," Obstetrics & Gynecology, 77: 48-52 (1991).

Utada et al., "Monodisperse double emulsions generated from a microcapillary device," Science, 308: 537-541 (2005).

Yin et al., "Encapsulation and sustained release from biodegradable microcapsules made by emulsification/freeze drying and spray/freeze drying," J Colloid Interface Sci, 336: 155-161 (2009).

* cited by examiner

*Primary Examiner* — Marcela M Cordero Garcia
(74) *Attorney, Agent, or Firm* — Casimir Jones S.C.

(57) ABSTRACT

The present invention relates to assembly of peptide amphiphiles and biopolymers into fibrous microcapsules, and uses thereof. In particular, the present invention provides devices, compositions, and methods for interfacial self-assembly of peptide amphiphiles and biopolyments into fibrous microcapsules, and uses thereof.

12 Claims, 8 Drawing Sheets

FIBROUS MICROCAPSULES AND METHODS OF ASSEMBLY AND USE THEREOF

This application claims priority to U.S. Provisional Patent Application Ser. No. 61/345,419, filed May 17, 2010, which is herein incorporated by reference in its entirety.

STATEMENT REGARDING FEDERALLY SPONSORED RESEARCH OR DEVELOPMENT

This invention was made with government support under DE-FG02-00ER45810 awarded by the Department of Energy. The government has certain rights in the invention.

FIELD OF THE INVENTION

The present invention relates to assembly of peptide amphiphiles and biopolymers into fibrous microcapsules, and uses thereof. In particular, the present invention provides devices, compositions, and methods for interfacial self-assembly of peptide amphiphiles and biopolymers into fibrous microcapsules, and uses thereof.

BACKGROUND OF THE INVENTION

Peptide amphiphiles (PA) are small, synthetic molecules composed of a hydrophobic alkyl tail, a beta-sheet forming peptide sequence, a charged amino acid sequence and a short peptide segment usually containing a bioactive epitope (SEE FIG. 1A) (Hartgerink et al. PNAS 2002, 99, 5133-5138; Hartgerink et al. Science 2001, 294, 1684-1688; herein incorporated by reference in their entireties). Peptide amphiphiles assemble into high-aspect ratio nanofibers (SEE FIG. 1B) upon electrostatic screening of the charged amino acids. In vivo and in vitro studies have shown that certain PA molecules, such as those with IKVAV, RGD or VEGF epitopes, exhibit significant biological activity (Silva et al. Science 2004, 303, 1352-1355; Rajangam et al. Nano Lett. 2006, 6, 2086-2090; herein incorporated by reference in their entireties). PAs and oppositely charged polymers can self-assemble at the aqueous interface of two solutions into hierarchically organized, semipermeable membranes, producing sac-like structures on the macro scale ($\geq 1$ mm) (Capito et al. Science 2008, 319, 1812-1816; herein incorporated by reference in its entirety).

SUMMARY OF THE INVENTION

In some embodiments, the present invention provides a fibrous microcapsule composition comprising peptide amphiphiles and biopolymers. In some embodiments, the biopolymer comprises alginate. In some embodiments, the peptide amphiphiles and biopolymers self-assemble into fibrous microcapsules. In some embodiments, microcapsules are provided, which are produced by mixing of biopolymer microdroplets with peptide amphiphiles. In some embodiments, devices are provided for production of microcapsules.

In some embodiments, the present invention provides a method of producing fibrous microcapsules comprising: (a) producing nebulized biopolymer micordroplets; and (b) self-assembling of microdroplets into fibrous microcapsules. In some embodiments, self-assembling occurs spontaneously under the conditions used. In some embodiments, the biopolymer microdroplets comprise peptide amphiphiles and biopolymers. In some embodiments, a biopolymer is selected from collagen, chitosan, alginate, hyaluronic acid, poly-lactic acid, poly-glycolic acid, poly-caprolactone, and polyurethane. In some embodiments, the biopolymers comprise alginate.

In some embodiments, the present invention provides a nebulizer device for assembly of fibrous microcapsules comprising: (a) pressure microinjector; (b) glass capillary; and (c) compressed gas in coaxial flow. In some embodiments, the pressure microinjector provides delivery of biopolymer. In some embodiments, the glass capillary comprises a diameter between 20-100 µm.

In some embodiments, the present invention provides a fibrous microcapsule composition comprising peptide amphiphiles and biopolymers. In some embodiments, the biopolymer comprises alginate. In some embodiments, the biopolymer is selected from collagen, chitosan, alginate, hyaluronic acid, poly-lactic acid, poly-glycolic acid, poly-caprolactone, and polyurethane. In some embodiments, the microcapsule has a diameter of less than 100 µm. In some embodiments, the microcapsule has a diameter of less than 40 µm. In some embodiments, the present invention provides a composition comprising a plurality of the fibrous microcapsules having a coefficient of variation of about 20% or less.

In some embodiments, the present invention provides a method of producing fibrous microcapsules comprising: (a) forming microdroplets, wherein said microdroplets comprises one or more biopolymers; (b) placing said microdroplets into an aqueous peptide amphiphile solution; and (c) self-assembling of fibrous microcapsules from said microdroplets and peptide amphiphiles. In some embodiments, the self-assembling occurs spontaneously under the conditions used. In some embodiments, the biopolymers comprise alginate. In some embodiments, the biopolymer is selected from collagen, chitosan, alginate, hyaluronic acid, poly-lactic acid, poly-glycolic acid, poly-caprolactone, and polyurethane. In some embodiments, forming microdroplets comprises nebulizing one or more biopolymers in a nebulizer device.

In some embodiments, the present invention provides a fibrous microcapsule produced by the method comprising: (a) forming microdroplets, wherein said microdroplets comprises one or more biopolymers; (b) placing said microdroplets into an aqueous peptide amphiphile solution; and (c) self-assembling of fibrous microcapsules from said microdroplets and peptide amphiphiles. In some embodiments, the microcapsule has a diameter of less than 100 µm. In some embodiments, the microcapsule has a diameter of less than 40 µm. In some embodiments, the present invention provides a composition comprising a plurality of fibrous microcapsules of having a coefficient of variation of about 20% or less.

In some embodiments, the present invention provides fibrous microcapsules encapsulating a payload. In some embodiments, the payload is selected from proteins, small molecules, nucleic acids, cells, and therapeutics.

In some embodiments, the present invention provides a fibrous microcapsule composition comprising peptide amphiphiles and biopolymers. In some embodiments, the biopolymer comprises alginate. In some embodiments, the microcapsule has a diameter of less than 100 µm. In some embodiments, the microcapsule has a diameter of less than 40 µm. In some embodiments, the fibrous microcapsules have a coefficient of variation of about 20% or less.

In some embodiments, the present invention provides a method of producing fibrous microcapsules comprising: (a) forming microdroplets, wherein the microdroplets comprises one or more biopolymers; (b) placing the microdroplets into an aqueous peptide amphiphile solution; and (c) self-assembling of fibrous microcapsules from the microdroplets and peptide amphiphiles. In some embodiments, the self-assembling occurs spontaneously under the conditions used. In some embodiments, the biopolymers comprise alginate. In some embodiments, forming microdroplets comprises nebulizing one or more biopolymers in a nebulizer device. In some embodiments, the present invention provides a fibrous microcapsule produced by a) forming microdroplets, wherein the microdroplets comprises one or more biopolymers; (b) placing the microdroplets into an aqueous peptide amphiphile solution; and (c) self-assembling of fibrous microcapsules from the microdroplets and peptide amphiphiles.

In some embodiments, the present invention provides a nebulizing device for assembly of fibrous microcapsules comprising: (a) pressure microinjector; (b) biopolymer reservoir; (c) glass capillary; and (d) compressed gas in coaxial flow. In some embodiments, the glass capillary comprises a diameter between 20-100 μm. In some embodiments, the present invention comprises a system for production of microcapsules comprising: (a) a nebulizing device for assembly of fibrous microcapsules comprising: a pressure microinjector, a biopolymer reservoir, glass capillary, and compressed gas in coaxial flow; (b) a biopolymer, wherein the biopolymer is contained within the biopolymer reservoir; and (c) reservoir containing an aqueous peptide amphiphile solution. In some embodiments the present invention provides a method of producing microcapsules comprising: (a) mixing biopolymer and compressed gas within a nebulizing device; (b) ejecting biopolymer from the nebulizing device to produce biopolymer microdroplets; (c) placing the microdroplets into the reservoir containing an aqueous peptide amphiphile solution; and (d) self-assembling of peptide amphiphiles and microdroplets into fibrous microcapsules.

DETAILED DESCRIPTION OF THE INVENTION

The present invention relates to assembly of peptide amphiphiles and biopolymers into fibrous microcapsules, and uses thereof. In particular, the present invention provides devices, compositions, and methods for interfacial self-assembly of peptide amphiphiles and biopolyments into fibrous microcapsules, and uses thereof. Experiments conducted during development of embodiments of the present invention demonstrated production of microcapsules (MC) less than 100 μm in diameter (e.g., <20 μm).

Figure 4:
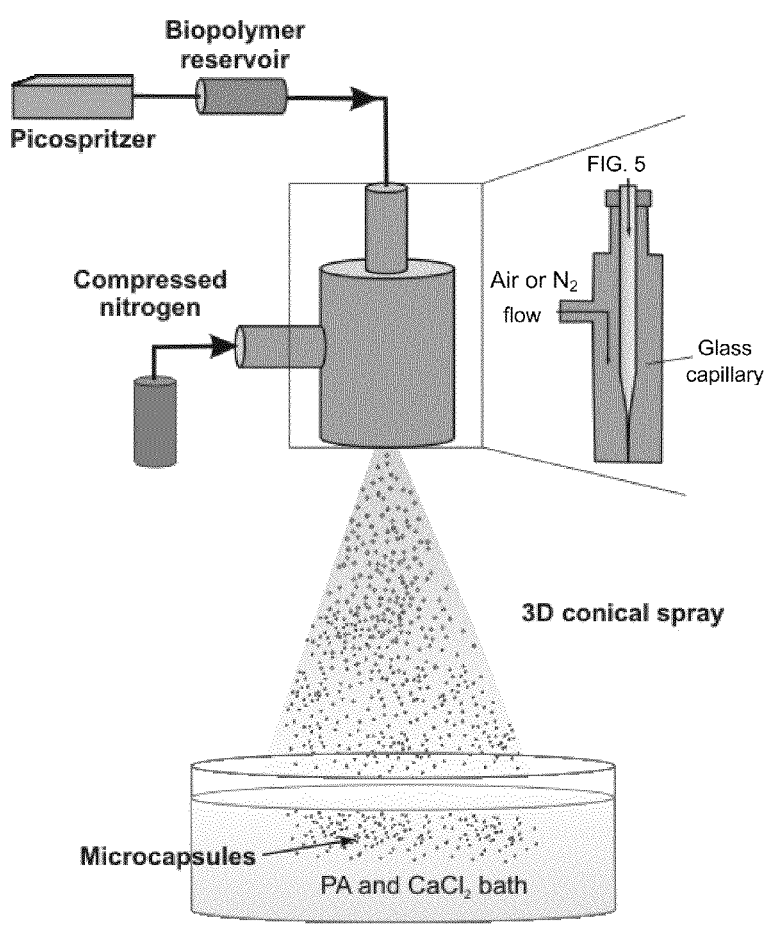
FIG. 4 shows schematic illustration of microcapsule/microbead formation using Capillary-PicoSpray droplet generator.

In some embodiments, MC formation proceeds via the generation of picoliter droplets of biopolymer. In some embodiments, the first step of MC formation utilizes the generation of picoliter droplets of biopolymer. In some embodiments, a spray-based device (e.g., nebulizer device) enables production of droplets with diameter ($d_{MC}$) as small as 15 μm and an average production rate $1 \cdot 10^8$ microcapsules per second (SEE FIG. 4). In some embodiments, the spraying nozzle consists of T-connector which connects the flow of compressed air or nitrogen with the polymer reservoir. In some embodiments, biopolymer (e.g. alginate) is dispensed through a glass capillary by the pump system. In some embodiments, the simultaneous flow of biopolymer (e.g., alginate) and high velocity gas ($N_2$) atomizes the polymer and the resulting microdroplets fall through the strainer (optional) into a collecting bath. In some embodiments, the Capillary-PicoSpray technique involves three operating steps for the production of microcapsules: 1) spraying of biopolymer (e.g., alginate) into the collecting bath, 2) separation/filtration of the microcapsules/microbeads from the solution of PA or PA with $CaCl_2$, 3) rinsing of microcapsules/beads. In some embodiments, polymer and gas flow rates, nozzle/capillary dimensions, and viscosity of the solutions are primarily responsible for the droplet size and shape. In some embodiments, a stream of 0.25 wt % aqueous alginate (AL) solution is nebulized by high-velocity flow of nitrogen. In some embodiments, microdroplets of biopolymer are directly ejected into an aqueous solution (e.g. 0.1 wt % aqueous solution of $C_{16}V_3A_3K_3$, 0.1 wt % aqueous solution of $C_{16}V_3A_3K_3$ with the addition of 2% $CaCl_2$, etc.). In some embodiments, after 15 minutes of assembly between PA and AL, MCs are centrifuged and thoroughly rinsed (e.g. with MilliQ water). In some embodiments, this method produces microdroplets uniform in size ($d_{MC}$~30 μm) and shape with a coefficient of variation CV ~20%. In some embodiments, a microfilter (e.g. a cell strainer) is inserted into the spraying line to optimize (e.g. reduce) the size range.

In some embodiments, microdroplets assemble into MCs. In some embodiments, microdroplets self-assemble into MCs. In some embodiments, microdroplets spontaneously assemble into MCs. In some embodiments, microdroplets spontaneously self-assemble into MCs.

A spray device or nebulizer device is provided in embodiments of the present invention. In some embodiments, nebulizers or atomizers employ compressed gas to produce microdroplets (See, e.g., DeVilbiss model 40 nebulizer). In some embodiments, nebulizers use ultrasonic vibrations (Hirabayashi & De la Mora (1998). Int. J. Mass Spectrom Ion Processes 175, 277-282; herein incorporated by reference in its entirety) and high pressure to produce microscopic droplets of solution. In some embodiments, a nebulizer device employs one or more of: (a) a pressure microinjector (e.g., for the delivery of biopolymer), (b) a glass capillary (e.g. orifice diameter 20-100 μm (e.g. ~40 μm)), and (c) compressed gas (e.g. argon, nitrogen, air, etc.) in the coaxial flow (SEE FIG. 4). In some embodiments, the nebulizer device employs each of: (a) a pressure microinjector for the delivery of biopolymer, (b) a glass capillary (e.g. orifice diameter 20-100 μm (e.g. ~40 μm)), and (c) compressed gas (e.g. nitrogen or air) in the coaxial flow. Exemplary nebulizer devices, elements of which may find use in embodiments of the present invention, are described, for example in: U.S. Pat. No. 7,905,228; U.S.

Pat. No. 7,905,228; U.S. Pat. No. 7,849,851; U.S. Pat. No. 7,267,120; and U.S. Pat. No. 7,332,286.

In some embodiments, droplets of biopolymer with diameter ($d_{MC}$) less than 200 µm (e.g., <100 µm, <75 µm, <50 µm, <40 µm, <30 µm, <20 µm, <10 µm, or less) are produced by any suitable technique (e.g., nebulizer device, atomizer, sonication, mixing, combinations thereof, etc.). In some embodiments, droplets of biopolymer have an average diameter less than 200 µm (e.g., <100 µm, <75 µm, <50 µm, <40 µm, <30 µm, <20 µm, <10 µm, or less). In some embodiments, a composition comprising droplets of biopolymer are filtered to produce a composition comprising droplets of biopolymer with diameter <200 µm, <100 µm, <75 µm, <50 µm, <40 µm, <30 µm, <20 µm, <10 µm, etc. In some embodiments, suitable methods of biopolymer production provide rapid droplet production (e.g., an average production rate $1 \cdot 10^8$ microcapsules per second (MCps). In some embodiments, biopolymer droplets are produced (e.g., via a nebulizer or other method or device) at a production rate of greater than $1 \sim 10^5$ MCps (e.g., $>1 \cdot 10^5$ MCps, $>1 \cdot 10^6$ MCps, $>1 \cdot 10^7$ MCps, $>1 \cdot 10^8$ MCps, $>1 \cdot 10^9$ MCps, $>1 \cdot 10^{10}$ MCps, or more). In some embodiments biopolymer droplets are produced (e.g., via a nebulizer or other method or device) at an average production rate of $1 \cdot 10^8$ MCps (SEE FIG. 4).

In some embodiments, the present invention provides microdroplets and microcapsules comprising one or more biopolymers. In some embodiments, a suitable biopolymer comprises alginic acid, also called algin or alginate. Alginic acid is a linear polysaccharide obtained from brown algae and seaweed and consist of -1,4-linked glucuronic and mannuronic acid units. As used herein, the term "alginate" refers to a polyanionic polysaccharide copolymer derived from sea algae (e.g., *Laminaria hyperborea, L. digitata, Eclonia maxima, Macrocystis pyrifera, Lessonia nigrescens, Ascophyllum codosum, L. japonica, Durvillaea antarctica*, and *D. potatorum*) and which includes -D-mannuronic (M) and -L-guluronic acid (G) residues in varying proportions. An alginate suitable for use in the present invention has a ratio between -L-guluronic acid and -D-mannuronic preferably ranging between 1:1 to 3:1 (e.g., 1.5:1, 2.5:1, about 2), and/or has a molecular weight ranging preferably between 1 to 1,000 kDa (e.g., 5 to 750 kDa, 10 to 500 kDa, 20 to 100 kDa, etc.).

In some embodiments, a suitable biopolymer is selected from collagen, chitosan, alginate, hyaluronic acid, poly-lactic acid, poly-glycolic acid, poly-caprolactone, and polyurethane. In some embodiments, a biopolymer comprises repeating monomer units. Nonlimiting suitable biopolymers include synthetic polymers such as polyalkylene oxides including poly(ethylene glycol), poly(ethylene oxide), and poly(ethylene oxide)-co-poly(propylene oxide) block copolymers (poloxamers and meroxapols), partially or fully hydrolyzed poly(vinyl alcohol), poly(vinylpyrrolidone), poly (ethyloxazoline), poloxamines, carboxymethyl cellulose, and hydroxyalkylated celluloses such as hydroxyethyl cellulose and methylhydroxypropyl cellulose; and natural polymers such as polypeptides, polysaccharides or carbohydrates such as FICOLL, polysucrose, hyaluronic acid, dextran, heparan sulfate, chondroitin sulfate, heparin, or alginate; and proteins such as gelatin, collagen, albumin, or ovalbumin or copolymers or combinations thereof. As used herein, "celluloses" includes cellulose and derivatives of the types described above; "dextran" includes dextran and similar derivatives thereof.

Other suitable polymers for use in embodiments of the present invention include modified alginates. As used herein, the term "modified alginates" refers to chemically modified alginates (e.g., with modified properties). Naturally occurring alginate may be chemically modified to produce alginate polymer derivatives that, for example, degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel and the alginate polymers may be derivatized with hydrophobic, water-labile chains, e.g., oligomers of epsilon-caprolactone.

Other polymeric compositions which may be utilized as biopolymers in embodiments of the present invention include: polyethylene oxide-polypropylene glycol block copolymers such as PLURONICS or TETRONIC, as described in Steinleitner et al., Obstetrics & Gynecology, vol. 77, pp. 48-52 (1991); and Steinleitner et al., Fertility and Sterility, vol. 57, pp. 305-308 (1992); both of which are incorporated herein by reference in their entireties. Other materials which may be utilized include proteins such as fibrin, collagen and gelatin. Polymer mixtures may also be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) can be combined to form a gel over the course of time, e.g., as quickly as within a few seconds.

In some embodiments, the spraying nozzle of a nebulizer device comprises a T-connector which connects the flow of compressed gas (e.g., air, argon, nitrogen, etc.) with the biopolymer reservoir (e.g., alginate reservoir). In some embodiments, the spraying nozzle comprises a mixing chamber connecting the flow of compressed gas (e.g., air, argon, nitrogen, etc.) with the biopolymer reservoir (e.g., alginate reservoir). In some embodiments, the spraying nozzle of a nebulizer device comprises a Y-connector which connects the flow of compressed gas (e.g., air, argon, nitrogen, etc.) with the biopolymer reservoir (e.g., alginate reservoir). In some embodiments, biopolymer and gas are mixed within the nebulizer (e.g., nozzle, mixing chamber, connector, capillary, etc.) in a suitable manner to atomize the polymer, thereby resulting in the formation of microdroplets. In some embodiments, biopolymer microdroplets are size-sorted to select optimally sized microdroplets (e.g., sorting out microdroplets that are too large (e.g., >100 μm diameter and/or too small (e.g., <1 μm diameter). In some embodiments, microdroplet sorting is performed by any suitable method (e.g., size exclusion screen, size exclusion membrane, filtration, centrifuge, etc.). In some embodiments, microdroplets are collected in a collection bath of a suitable solution (e.g., PA solution, Pa and salt (e.g., $CaCl_3$)).

In some embodiments, microdroplet size (e.g., diameter) and shape (e.g., sphere, ovular, elongate, cylindrical, combinations thereof, etc.) are affected by one or more production factors, including: polymer flow rate, gas flow rate, type of polymer (e.g., alginate, collagen, etc.), concentration of polymer (e.g., 0.05 wt % 0.10 wt %, 0.15 wt %, 0.20 wt %, 0.25 wt %, 0.30 wt %, 0.35 wt %, 0.40 wt %, 0.50 wt %, or greater.), polymer solvent (e.g., aqueous solution (e.g., (e.g. $C_{16}V_3A_3K_3$ solution, $C_{16}V_3A_3K_3$ solution, etc.)), nozzle shape, nozzle dimensions, capillary dimensions, solution viscosity, etc. In some embodiments, the above production factors are adjusted to produce microdroplets of desired shape, size ($d_{MC}$~10 μm ... $d_{MC}$~20 μm ... $d_{MC}$~30 μm ... $d_{MC}$~40 μm ... $d_{MC}$~50 μm, etc.), and uniformity (e.g., coefficient of variation (CV) less than 50% (e.g., CV<40%, CV<30%, CV<20%, CV<10%, etc.). In some embodiments, a microfilter (e.g. a cell strainer) is inserted into the spraying line to optimize (e.g. reduce) the size range.

Figure 5:
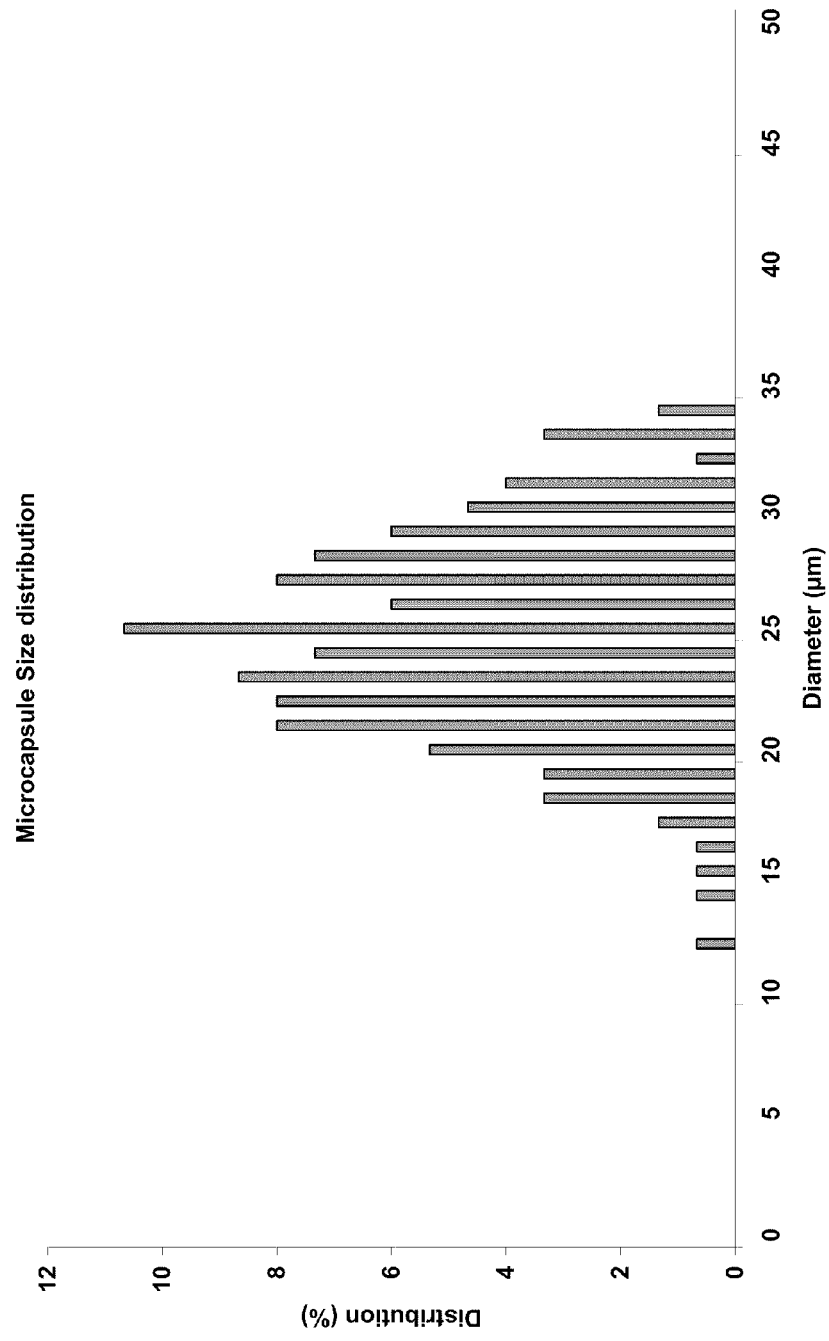
FIG. 5 shows PA-AL microcapsule size distribution histogram.

Experiments were performed during development of embodiments of the present invention to analyze the surface morphology, cross section, shape and uniformity of MCs. In some embodiments scanning electron microscopy (SEM), focused ion beam (FIB), optical microscopy, and fluorescence microscopy were used to analyze the surface morphology, cross section, shape and uniformity of MCs. Prior to SEM imaging, MCs were prepared by critical point drying processing (CPD) and osmium coating. In some embodiments, MCs have membranous, semipermeable shells with high surface area and fibrous exterior (SEE FIG. 2A, B). In some embodiments, the length of surface nanofibers exceeds 10 μm (e.g. 11 μm, 12 μm, μm 13 μm ... 20 μm ... 25 μm ... 30 μm ... 35 μm ... 40 μm) (SEE FIG. 2B, inset and FIG. 5). In some embodiment, typical surface nanofibers are approximately 2-3 μm. In some embodiments, nanofibers have diameters of 20 nm or less (e.g. 1 nm ... 2 nm ... 5 nm ... 10 nm ... 15 nm ... 20 nm).

Figure 1:
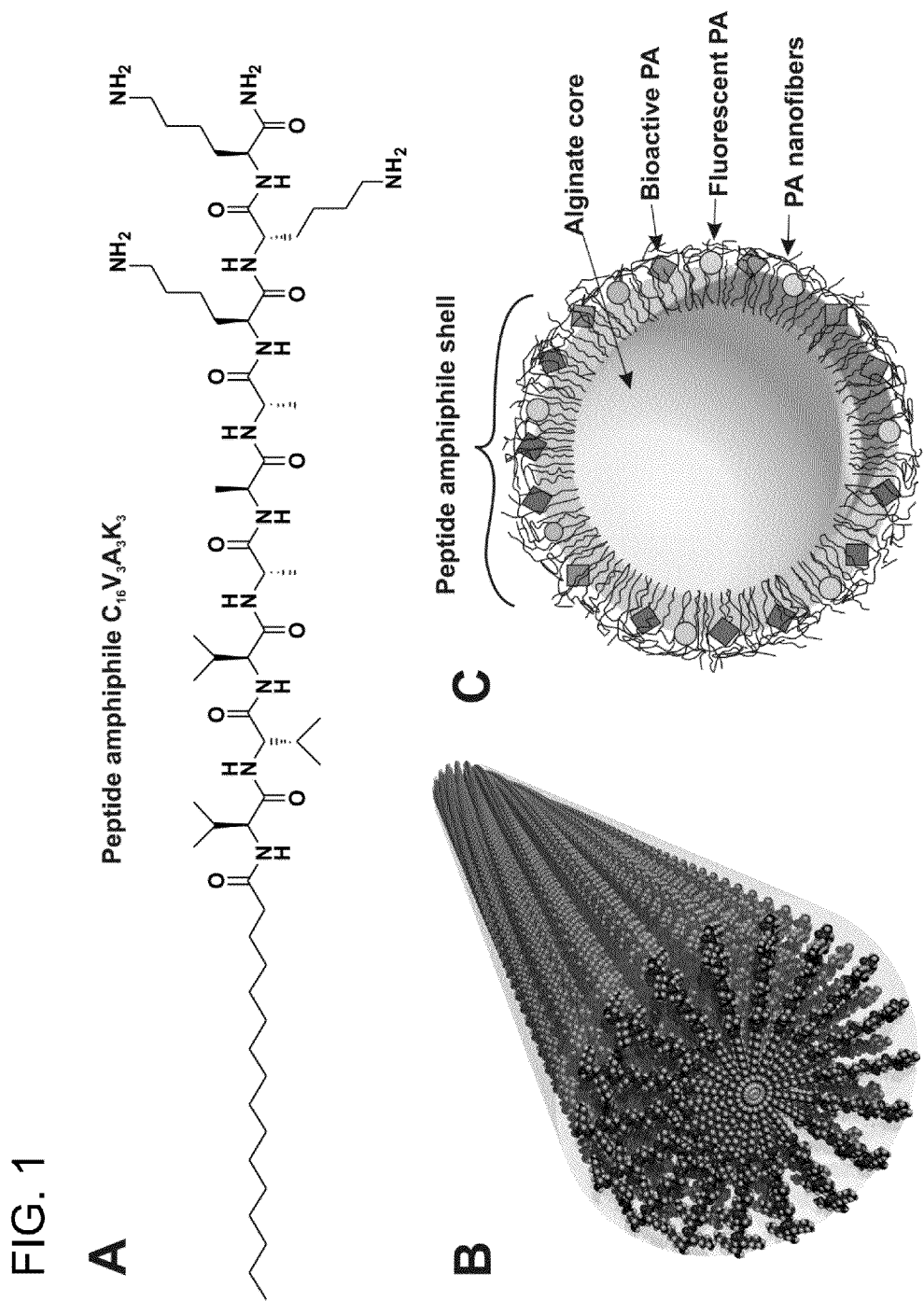
FIG. 1 shows (A) the molecular structure of peptide amphiphile $C_{16}V_3A_3K_3$; (B) molecular graphics of peptide amphiphile nanofiber; and (C) schematic illustration of cross section of PA-alginate microcapsule.
Figure 2:
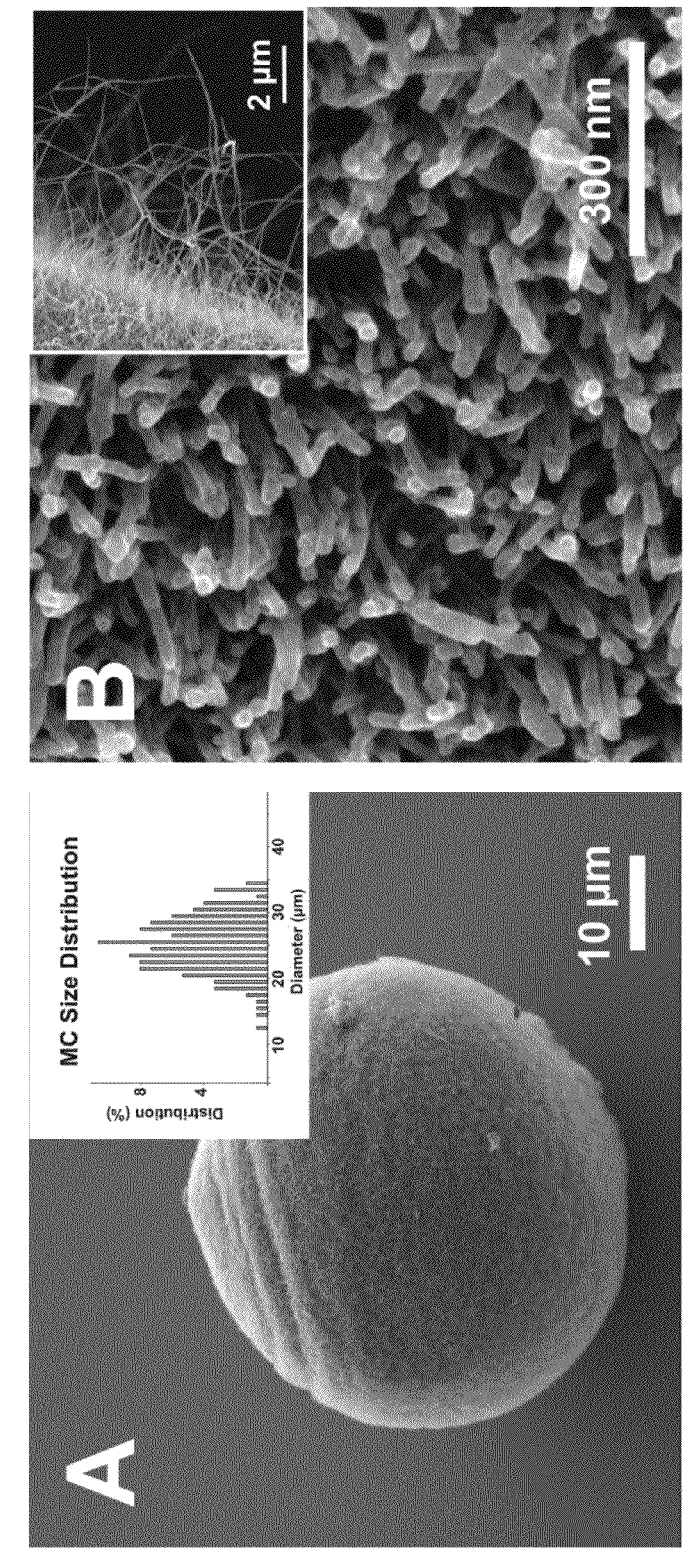
FIG. 2 shows SEM images of (A) PA-AL microcapsule; (B) top and side view (inset) of PA nanofibrous surface of the MC; (C) liquid-core MC (diameter ~1 mm) fractured to examine the interior, the inset shows a cross section of the capsule membrane; and (D) gel-filled MC cross-sectioned by FIB to investigate the morphology of the inner core. Inset represents zoom-in on the cross-linked alginate interior of MC.
Figure 2:
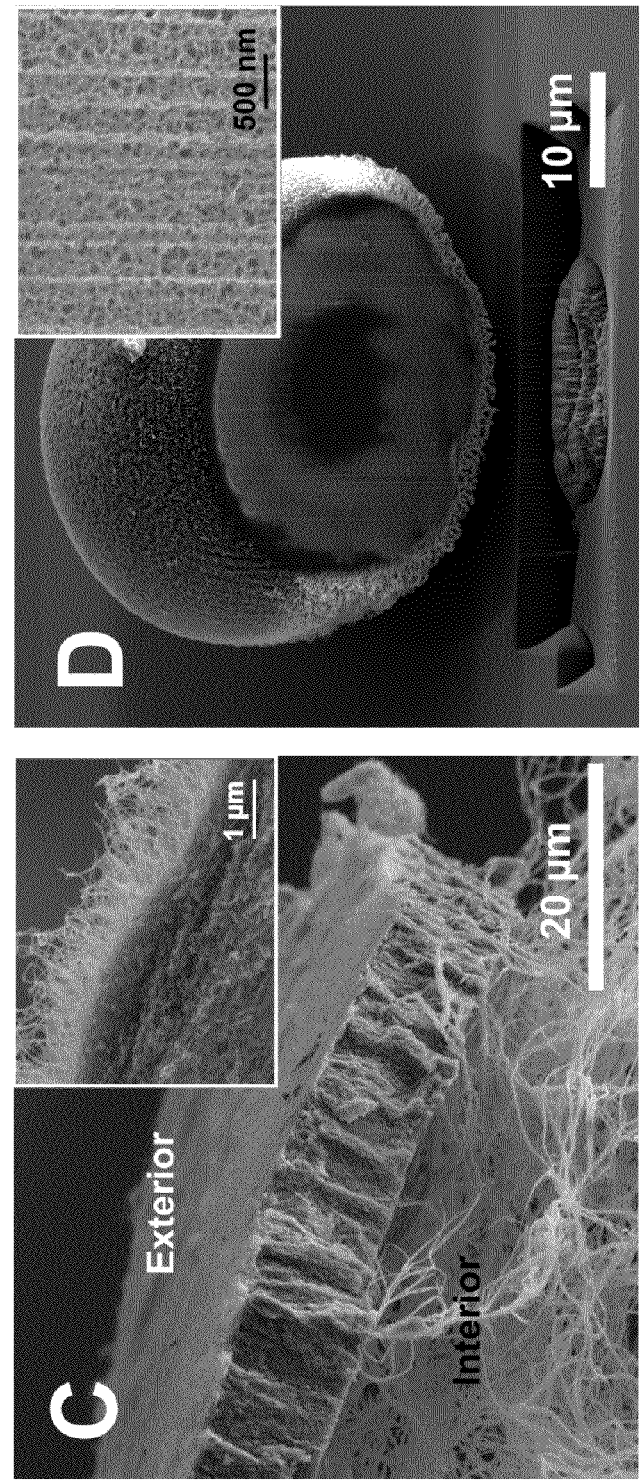

In some embodiments, PA-MCs have either a liquid or gel core (SEE FIG. 2C, D). In some embodiments, the addition of divalent metal ions assists in providing a gel core. In some embodiments, a gel core is formed by cross-linking biopolymer (e.g., alginate) with, e.g. $Ca^{2+}$, either during or after MC formation. In some embodiments, core gelation enables the formation of mechanically stable structures demonstrating resistance to damage during processing (e.g. rinsing, centrifuging, and handling). In some embodiments, liquid core capsules are more susceptible to collapse and burst than gel core capsules. In some embodiments, the gelation process can be reversed by the addition of chelating agent solution, e.g. sodium citrate. During development of embodiments of the present invention, to investigate the interior of liquid-core capsules, ~1 mm capsules were prepared and fractured with tweezers before SEM imaging (SEE FIG. 2C). In some embodiments, before SEM measurements, samples were dehydrated by the exchange with ethanol of increasing concatenation (10%-100% of ethanol). In some embodiments, MCs were immersed in each solution for at least 10 min (e.g. 10 min in 10, 20, 30 etc. and finally in 100% ethanol). In some embodiments, ethanol was removed by critical point drying (CPD). Large (~1 mm) liquid core MCs were cut-open with tweezers prior SEM measurements. Smaller liquid core MCs (<100 μm) usually collapsed during CPD processing while gel-core MCs remain spherical shape. 8 nm of osmium was deposited with an osmium plasma coater onto dry MCs in order to minimize electron beam charging during imaging of organic structures. In some embodiments, liquid-filled MCs have a well defined membrane comprising an amorphous inner layer of biopolymer and an outer layer of PA nanofibers (SEE FIG. 2C inset). In some embodiments, this morphology is representative of osmotic pressure driven membrane formation mechanism (1). During development of embodiments of the present invention, Gel-core MCs were prepared by CPD and cross-sectioned by FIB/SEM to study the interior morphology and the structure of the membrane (SEE FIG. 2D). In some embodiments, gel-core capsules have a sponge-like interior structure and the exterior exhibits nanofibrous morphology.

Figure 3:
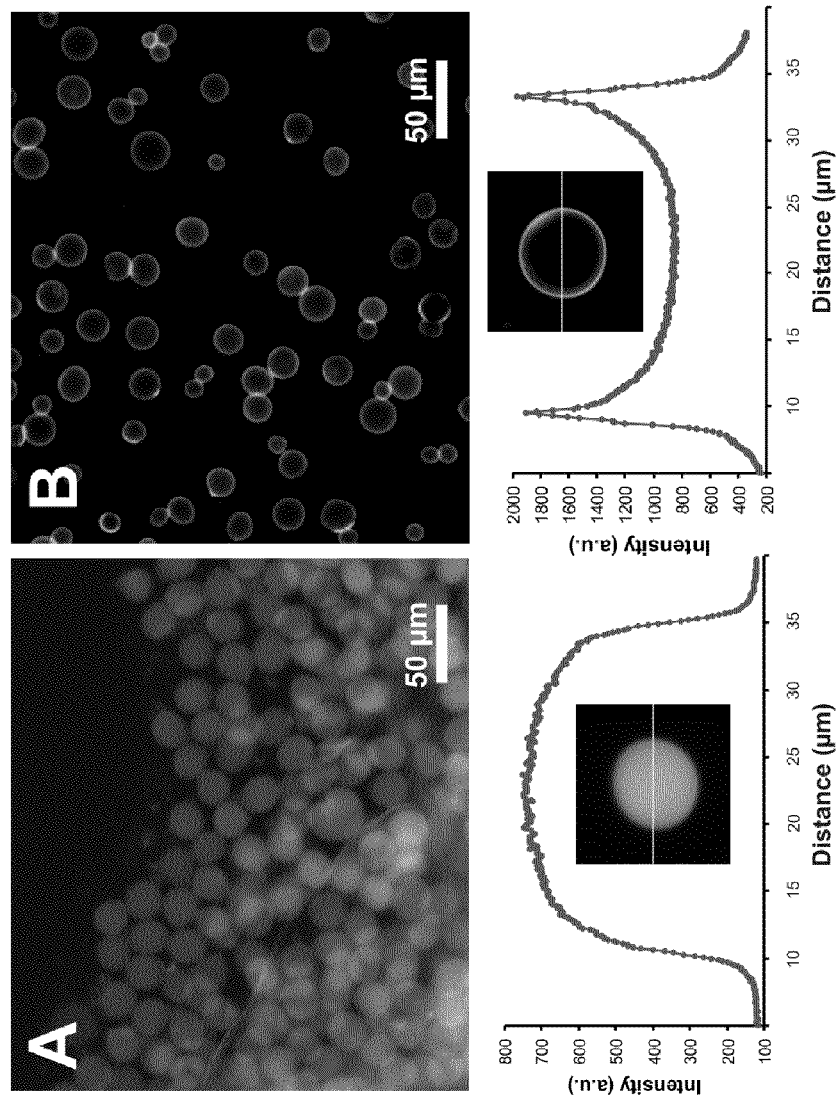
FIG. 3 shows fluorescence microscopy and fluorescent intensity profile of PA-AL microcapsules (A) with encapsulated FITC-BSA (B) containing FITC-labeled PA in its shell.
Figure 6:
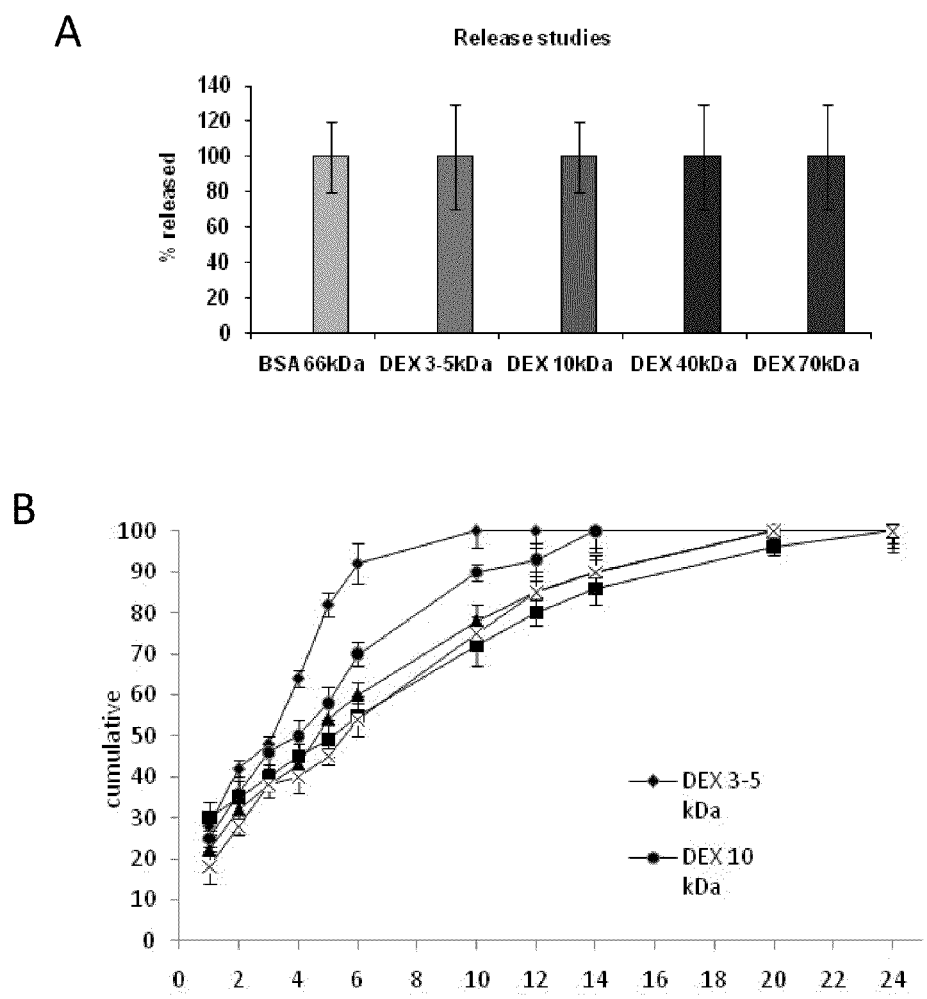
FIGS. 6A and 6B show data generated by dextran and BSA release studies from PA-AL microcapsules in PBS over 24 h.
Figure 7:
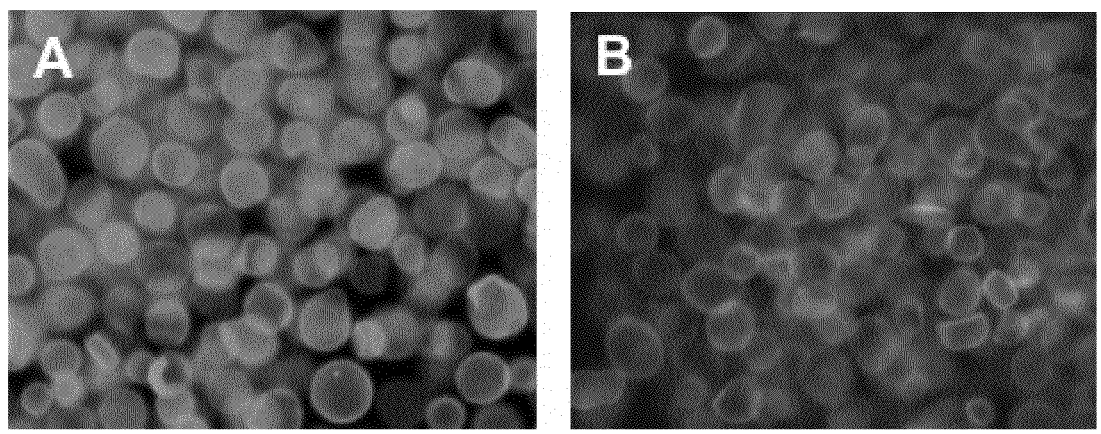
FIG. 7 shows fluorescence microscopy images of PA/AL microcapsules with encapsulated (A) FITC-BSA, (B) FITC-dextran 3-5 kDa.

In some embodiments, compositions of the present invention (MCs) are configured encapsulate and/or release proteins (e.g., for biomedical applications). In some embodiments, MCs are generated with varying encapsulation and release characteristics. During development of embodiments of the present invention, membrane permeability was evaluated to characterize release properties of the MCs. Membrane permeability was evaluated with UV-Vis spectrometry and fluorescence microscopy using fluorescein isothiocyanate (FITC) labeled dextrans (3-70 kDa) and FITC labeled bovine serum albumin (BSA). In some embodiments, the release of standard fluorescein isothiocyanate dextran and bovine serum albumin molecules from the PA-AL microcapsule was examined. FITC-labelled dextran with molecular weight of 3-5 kDa, 10 kDa, 40 kDa and 70 kDa as well as FITC-BSA was used. Five different spraying solutions were prepared; each was a mixture of 1 mg/ml PBS solution of FITC labeled dextran molecular weight standards (3-5 kDa, 10 kDa, 40 kDa, 70 kDa and FITC-BSA) with 0.5% alginate. The solutions were sprayed into 0.1% $C_{16}V_3A_3K_3$ containing 2% $CaCl_2$. The resulting MCs were rinsed with $H_2O$ and PBS and transferred into the releasing medium (PBS pH 7.4) at 37° C. for 24 hours. The encapsulation of fluorescent dextrans and BSA was investigated with fluorescence microscopy. The FITC-BSA and dextran encapsulated MCs exhibited strong fluorescence, which was uniform across the entire MC (SEE FIG. 3A). After release of FITC-BSA and dextrans, no fluorescence signal was observed from the MCs. The concentration of released standard molecules in PBS was measured with UV-Vis spectrometry. Complete release of all dextran (3-70 kDa) and BSA molecules was observed after 24 hours in PBS (SEE FIG. 6).

In some embodiments, PA microcapsules provide a flexible platform for surface functionalization through the introduction of reactive epitopes or tags linked via covalent bonds in the PA structure. In some embodiments, a fluorescent marker is incorporated in the exterior of the microcapsule by mixing FITC labeled PA ($C_{16}V_3A_3K_3$-FITC) with $C_{16}V_3A_3K_3$ (1:100 by weight ratio, total concentration 0.1%) prior to spraying of 0.25% alginate microdroplets (SEE FIG. 3B). Experiments, conducted during development of embodiments, of the present invention demonstrated that membrane of fluorescein-MCs showed clear fluorescent edge contrast (SEE FIG. 3B) indicating successful co-self-assembly of FITC-PA with PA and AL. This type of functionalization offers a straightforward approach for the incorporation of specific fluorescent tags into the MC wall which may facilitate, e.g., in vivo tracking of MCs using fluorescence imaging techniques.

In some embodiments, the present invention provides, a simple process for the fabrication of microcapsules with tunable surface functionality via spontaneous self-assembly of small, positively charged peptide amphiphile molecules and negatively charged, high molecular weight biopolymer (e.g., alginate). In some embodiments, the PA-nanofibrous microcapsules exhibit unique morphology and release properties. In some embodiments, functional tags such as FITC can be covalently incorporated in the PA molecule and co-self-assembled with $C_{16}V_3A_3K_3$ and biopolymer (e.g., alginate) into the membrane structure. In some embodiments self-assembled peptide amphiphile capsules find use in targeted controlled drug release, cancer therapies, functional biomedical materials, as well as in the cosmetic and biotech industries.

In some embodiments, microcapsules of the present invention find use in the fields of research, medicine, materials, etc. In some embodiments, microcapsules provide a delivery platform for therapeutics or other small molecule, protein, cellular, biomolecular, and/or nucleic acid payloads. In some embodiments, microcapsules provide a scaffold for attachment of other function groups. In some embodiments, microcapsules stably encapsulate a payload (e.g., small molecules, proteins, nucleic acids, biomolecules, cells, carbohydrates, therapeutics, etc.). In some embodiments, microcapsules provide release (e.g., timed release, predictable release rate, etc.) of an encapsulated payload (e.g., small molecules, proteins, nucleic acids, carbohydrates, biomolecules, cells, therapeutics, etc.).

EXPERIMENTAL

The 0.25 wt % alginate solution (HF 120 RBS from FMC Biopolymers, G/M (%) 45-55/45-55, $M_w$=300-400 kDa.) was introduced into the Cole-Palmer silicon tubing system of Picospritzer III (General Valve/Parker Hannifin). A glass capillary was then attached to the outlet of the tubing. Spraying of microdroplets of biopolymer solution was performed by the simultaneous polymer and air flow. The droplets of biopolymer were ejected into the aqueous solution of 0.1 wt % PAs ($C_{16}V_3A_3K_3$) or PAs containing 2% $CaCl_2$ (for the gel-filled microcapsules). The pressure microinjector was set to 45 psi in all experiments. The microdroplets were passed through the strainer (pore diameter <40 μm). The solution of PAs was stirred continuously by a magnetic stirrer (with optionally cooling or heating). Once microcapsules/microbeads were formed, they were removed from the solution, passed through the strainer again, washed and centrifuged. The droplets were re-suspended in saline solution (0.9% NaCl), PBS or water. PA microcapsules were stored in saline or MilliQ water for weeks without any change in its structure or composition. Peptide amphiphiles ($C_{16}V_3A_3K_3$) were synthesized at IBNAM Chemical Core. Alginate HF 120 RBS, $M_w$=300-400 kDa was purchased from FMC Biopolymers, (G/M (%) 45-55/45-55, 1 wt % sol., 20° C. is 600-800 mPas). Silicon tubing was purchased from Cole Palmer. Glass capillaries were purchased from Sutter Instrument Co. Strainers with pore diameter of 40 μm were purchased from BD Falcon. FITC-BSA was purchased from Molecular Probes. $CaCl_2$, NaCl, fluorescein isothiocyanate dextrans, sodium citrate and other chemicals were purchased from Sigma Aldrich.

All publications and patents in the present application and/or listed below are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

REFERENCES

1. Capito, R. M.; Azevedo, H. S.; Velichko, Y. S.; Mata, A.; Stupp, S. I., Science 2008, 319, 1812-1816.
2. Chang, T. M. S., Science 1964, 146, 524-525.
3. Decher, G., Science 1997, 277, 1232-1237.
4. Caruso, F.; Caruso, R. A.; Mohwald, H., Science 1998, 282, 1111-1114.
5. Donath, E.; Sukhorukov, G. B.; Caruso, F.; Davis, S. A.; Mohwald, H., Angew. Chem. Int. Ed. 1998, 37, 2202-2205.
6. Kamio, E.; Yonemura, S.; Ono, T.; Yoshizawa, H., Langmuir 2008, 24, 13287-13298.
7. Yin, W. S.; Yates, M. Z., J. Colloid Interface Sci. 2009, 336, 155-161.
8. Kenis, P. J. A.; Ismagilov, R. F.; Whitesides, G. M., Science 1999, 285, 83-85.
9. Utada, A. S.; Lorenceau, E.; Link, D. R.; Kaplan, P. D.; Stone, H. A.; Weitz, D. A., Science 2005, 308, 537-541.
10. Hartgerink, J. D.; Beniash, E.; Stupp, S. I., PNAS 2002, 99, 5133-5138.
11. Hartgerink, J. D.; Beniash, E.; Stupp, S. I., Science 2001, 294, 1684-1688.
12. Silva, G. A.; Czeisler, C.; Niece, K. L.; Beniash, E.; Harrington, D. A.; Kessler, J. A.; Stupp, S. I., Science 2004, 303, 1352-1355.
13. Rajangam, K.; Behanna, H. A.; Hui, M. J.; Han, X. Q.; Hulvat, J. F.; Lomasney, J. W.; Stupp, S. I., Nano Lett. 2006, 6, 2086-2090.

We claim:

1. A fibrous microcapsule composition comprising a fibrous outer shell of peptide amphiphiles and a spherical biopolymer core, wherein said peptide amphiphiles comprise a hydrophobic tail, a beta-sheet forming peptide, a charged amino acid sequence, and a short peptide segment.

2. The fibrous microcapsule composition of claim 1, wherein said biopolymer core comprises alginate.

3. The fibrous microcapsule composition of claim 1, wherein said microcapsule has a diameter of less than 100 μm.

4. The fibrous microcapsule composition of claim 3, wherein said microcapsule has a diameter of less than 40 μm.

5. A composition comprising a plurality of the fibrous microcapsules of claim 1, wherein said fibrous microcapsules have a coefficient of variation of about 20% or less.

6. A method of producing the fibrous microcapsules of claim 1 comprising:
(a) forming microdroplets, wherein said microdroplets comprises one or more biopolymers;
(b) placing said microdroplets into an aqueous solution of peptide amphiphiles, wherein said peptide amphiphiles comprise a hydrophobic tail, a beta-sheet forming peptide, a charged amino acid sequence, and a short peptide segment; and
(c) self-assembling of fibrous microcapsules from said microdroplets and peptide amphiphiles.

7. The method of claim 6, wherein self-assembling occurs spontaneously under the conditions used.

8. The method of claim 6 wherein said biopolymers comprise alginate.

9. The method of claim 6, wherein said forming microdroplets comprises nebulizing one or more biopolymers in a nebulizer device.

10. A composition comprising a microcapsule of claim 1 further encapsulating a payload.

11. The composition of claim 10, wherein said payload is selected from proteins, small molecules, nucleic acids, cells, and therapeutics.

12. A method of producing microcapsules of claim 1 comprising:
(a) mixing a biopolymer and a compressed gas within a nebulizing device, the nebulizing device comprising:
(i) a pressure microinjector;
(ii) a biopolymer reservoir;
(iii) a capillary; and
(iv) a compressed gas source;
(b) ejecting the biopolymer from said nebulizing device through said capillary to produce biopolymer microdroplets;
(c) placing said microdroplets into an aqueous solution of peptide amphiphiles; and
(d) allowing self-assembly of peptide amphiphiles and microdroplets into fibrous microcapsules.

* * * * *